United States Patent
Murinson et al.

(10) Patent No.: US 8,366,647 B2
(45) Date of Patent: Feb. 5, 2013

(54) APPARATUS AND METHOD FOR TREATING ULNAR NEUROPATHY

(75) Inventors: Beth B. Murinson, Baltimore, MD (US); Justin C. McArthur, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 612 days.

(21) Appl. No.: 11/794,595

(22) PCT Filed: Dec. 30, 2005

(86) PCT No.: PCT/US2005/047538
§ 371 (c)(1),
(2), (4) Date: Oct. 23, 2009

(87) PCT Pub. No.: WO2006/072029
PCT Pub. Date: Jul. 6, 2006

(65) Prior Publication Data
US 2010/0094187 A1    Apr. 15, 2010

Related U.S. Application Data

(60) Provisional application No. 60/640,691, filed on Dec. 30, 2004.

(51) Int. Cl.
*A61F 5/00*     (2006.01)
*A61F 13/00*    (2006.01)

(52) U.S. Cl. ............ 602/20; 602/61; 128/846; 128/869; 128/881

(58) Field of Classification Search ................ 602/5, 13, 602/20–23, 60–64, 26; D24/190, 191, 192
See application file for complete search history.

(56) References Cited

U.S. PATENT DOCUMENTS

| | | | |
|---|---|---|---|
| 4,084,586 A * | 4/1978 | Hettick | 602/60 |
| 4,938,207 A | 7/1990 | Vargo | |
| 5,514,081 A * | 5/1996 | Mann | 602/20 |
| 5,891,079 A * | 4/1999 | Barnes | 602/61 |
| D460,824 S * | 7/2002 | Ames | D24/190 |
| 8,719,711 | 4/2004 | Islava | |
| 2002/0165474 A1 * | 11/2002 | Chiang et al. | 602/26 |

* cited by examiner

*Primary Examiner* — Kim M Lewis
(74) *Attorney, Agent, or Firm* — Edwards Wildman Palmer LLP; Peter F. Corless; Lisa Swiszcz (57) ABSTRACT

An apparatus and method for treating ulnar neuropathy are disclosed. An apparatus for treating ulnar neuropathy includes an inner face for engaging an arm with an upper end terminating above the elbow and a lower end terminating below the elbow; a plurality of mechanical fasteners along an edge of the inner face; an outer face having channels to promote circumferential flexibility; and a plurality of mechanical fasteners on the outer face positioned to oppose the plurality of mechanical fasteners on the inner face. A method of treating ulnar neuropathy includes placing an inner face in contact with the arm; wrapping the device around the arm to extend above and below the elbow; engaging mechanical fasters on the inner face with mechanical fasteners on the outer face; and tightening the device to support the elbow while allowing normal circulation in the arm.

18 Claims, 6 Drawing Sheets

APPARATUS AND METHOD FOR TREATING ULNAR NEUROPATHY

RELATED APPLICATIONS

This application claims the benefit of U.S. Provisional Application Ser. No. 60/640,691, filed Dec. 30, 2004, the entirety of which is hereby incorporated herein by reference.

FIELD

The embodiments disclosed herein relate to devices for the treatment of ulnar neuropathy and more particularly to an apparatus and method for treating ulnar neuropathy.

BACKGROUND

Ulnar neuropathy is a condition involving impaired movement or sensation in the wrist and hand caused by damage to the ulnar nerve. Ulnar means pertaining to the hand, forearm and elbow and neuropathy means a disturbance to the peripheral nerve system. Ulnar neuropathy, or ulnar nerve dysfunction, is a form of peripheral neuropathy. Ulnar tunnel syndrome is a specific ulnar neuropathy. The ulnar nerve travels from the shoulder down the outside of the arm, supplying flexion to the wrist and aiding in movement and sensation of the wrist and hand, to the fourth and fifth fingers in particular. The ulnar nerve is near the surface of the body where it crosses the elbow, so prolonged pressure on the elbow or entrapment of the nerve may cause damage.

Ulnar neuropathy is a degeneration of the ulnar nerve. Ulnar neuropathy is marked by numbness, tingling, or pain in the arm and hand on the side of the little finger and the outer side of the palm. In addition to these sensory symptoms, in more advanced cases, weakness and loss of muscle in the hand may also occur. Elbow pain is frequent in this condition and many people will notice that touching their elbow the wrong way causes a sharp shooting pain to descend down the arm into the fingers.

Ulnar neuropathy can affect persons of any age, although it is more common in older individuals, after traumas, including fractures to the arm, and in individuals who lean on their elbows when speaking on the telephone or sitting in a chair with arms. Some conditions such as diabetic neuropathy can also predispose one to having ulnar neuropathy.

Causes of ulnar neuropathy include: prolonged external pressure on the nerve at the elbow, where the ulnar nerve is close to the surface of the body, or at the base of the palm; direct trauma, such as fracture or dislocation of the elbow; or compression of the nerve at the elbow or wrist from soft-tissue swelling, bone spurs, or damage to the myelin sheath that encases the nerve.

Ulnar neuropathy treatment may start conservatively with avoidance of postures that may injure the nerve. The patient should avoid using the hand, especially for activities involving small muscle movement of the hand, like typing and dialing the telephone. The patient may also wear a protective pad around the elbow.

Additional conservative treatments include simple nerve flexing exercises, nocturnal splinting or night-time braces to keep the arm straight, and medications to help alleviate symptoms and decrease swelling and pain, including anti-inflammatory medications and various forms of analgesics. In more extreme cases, steroids may be injected to reduce swelling and pressure on the nerve. If symptoms are unresponsive to more conservative treatment, or there is evidence of nerve degeneration, surgical intervention can be pursued.

Although there is solid evidence the ulnar neuropathy most often results from compression of the ulnar nerve, current treatments are not very effective and surgery is often the only resort for severely effected patients. The surgical procedure of choice is an ulnar transposition. As constant stretching and compression of the nerve is the culprit, simply moving the nerve to the superior medial aspect of the elbow is often sufficient in stopping pain. This transposing of the nerve will often stop further muscle wasting as well, but atrophy present in the hand may be irreversible. Surgery for the ulnar nerve is complex and the outcome, in terms of relief of symptoms and improvement in strength, is often not as good.

Use of an elbow splint at night will keep the elbow from being bent during sleep. Splint application alone may be adequate to improve the symptoms and ulnar nerve conduction across the elbow. A pad around the elbow during the day will protect the nerve from trauma. The pads are often elbow pads or guards that are used for sports and available from sporting goods stores. Splint and elbow pads may also be custom made by a hand therapist, a specialist center or a physical therapist. These interventions have little proven efficacy, can be expensive, and lack credibility in the patients' view.

Examples of elbow orthosis, pads, protectors and braces are known in the art. U.S. Pat. No. 6,730,052 discloses an elbow brace for supporting a person's elbow in a desired, fixed position comprising a sleeve, a pocket formed in the sleeve, a single pad enclosed within the pocket, and a pair of straps extending from the sleeve. U.S. Pat. No. 5,569,172 discloses an orthopedic pillow device for supporting and immobilizing a patient's arm relative to a patient's shoulder comprising a portable, L-shaped, reversible, pillow and a plurality of straps for attaching and securing the pillow to both the patient's upper torso and arm. U.S. Pat. No. 5,514,081 discloses an elbow orthosis having an inflatable bladder support and method of use. U.S. Pat. No. 6,551,280 discloses therapeutic devices and systems that provide support or pressure to tissue.

Thus, there is a need in the art for an apparatus and method for treating ulnar neuropathy that is effective, safe, comfortable, affordable and readily available.

SUMMARY

An apparatus and method for treating ulnar neuropathy is disclosed herein. According to aspects illustrated herein, there is provided an apparatus for treating ulnar neuropathy comprising: an inner face for engaging a person's arm with an upper end terminating above the person's elbow and a lower end terminating below the elbow; a plurality of mechanical fasteners along an edge of the inner face; an outer face having channels to promote circumferential flexibility; and a plurality of mechanical fasteners on the outer face positioned to oppose the plurality of mechanical fasteners on the inner face; wherein the apparatus is contoured to the shape of the elbow and maintains the elbow at a carrying angle less than about 180 degrees.

According to aspects illustrated herein, there is provided an apparatus for supporting an elbow in a desired position comprising: an inner face for engaging a person's arm with an upper end terminating above the person's elbow and a lower end terminating below the elbow; at least one hook and loop fastener located along an edge of the inner face; a plurality of channels in the inner face to provide support along a length of the inner face; and an outer face having channels to promote circumferential flexibility and at least one hook and loop fastener positioned to oppose the least one hook and loop fastener on the inner face; wherein the apparatus is contoured to the shape of the elbow and provides semi-rigid immobilization of the elbow.

According to aspects illustrated herein, there is provided a method of treating ulnar neuropathy comprising: placing an inner face of a device in contact with an arm of a patient; wrapping the device around the arm to extend above and below the elbow; engaging mechanical fasters on the inner face of the device with mechanical fasteners on the outer face; and tightening the device to apply pressure to the elbow while allowing normal circulation in the arm.

BRIEF DESCRIPTION OF THE DRAWINGS

The presently disclosed embodiments will be further explained with reference to the attached drawings, wherein like structures are referred to by like numerals throughout the several views. The drawings are not necessarily to scale, the emphasis having instead been generally placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
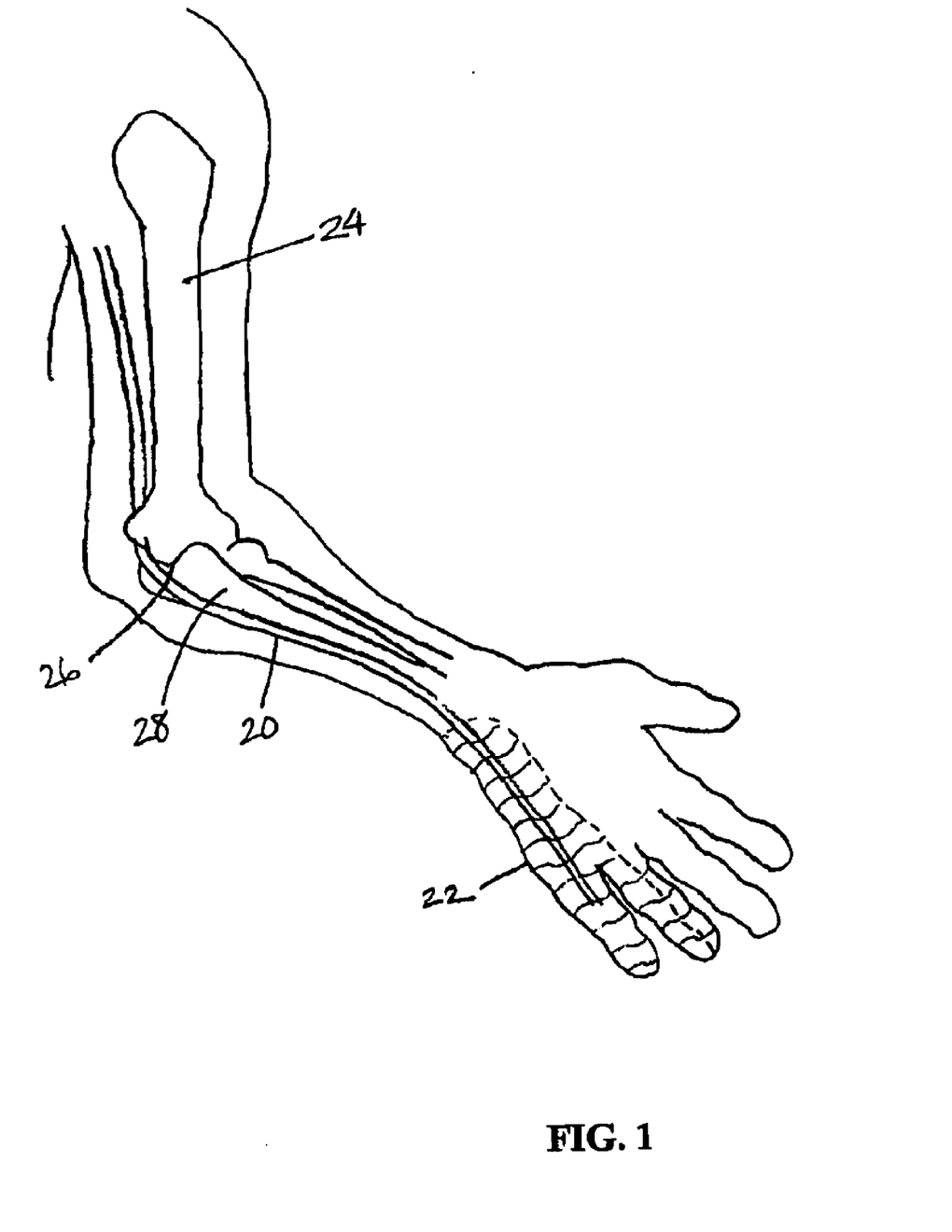
FIG. 1 shows a view of an arm showing the ulnar nerve and an area of numbness, pain or tingling often associated with ulnar neuropathy.

An apparatus and method for treating ulnar neuropathy is disclosed herein. FIG. 1 shows a view of an arm showing an ulnar nerve 20 and an area of numbness, pain or tingling 22 often associated with ulnar neuropathy. In humans, the ulnar nerve runs down the arm and forearm and into the hand. The ulnar nerve is formed from spinal nerve roots C8 and T1, which give rise to the medial cord which in turn, forms the ulnar nerve. The ulnar nerve comes from the lower cord of the brachial plexus, and runs posterior to a humerus 24 down the arm, going behind the medial epicondyle at an elbow joint 26. This part of the ulnar nerve is known as the funnybone. The ulnar nerve enters the anterior (front) side of the forearm, and runs alongside an ulna 28. The ulnar nerve innervates (supplies) one and a half muscles in the forearm: flexor carpi ulnaris (which flexes and adducts the wrist), and the medial two digits of flexor digitorum profundis (a muscle that flexes the fingers).

After the ulna, the ulnar nerve enters the palm of the hand (passing above the flexor retinaculum), to supply most of the intrinsic muscles of the hand. Muscles in the hand innervated by the ulnar nerve include the medial two lumbrical muscles, the muscles of the hypothenar eminence (opponens digiti minimi, flexor digiti minimi and abductor digiti minimi), the interossei (palmar and dorsal groups), the first dorsal interosseus muscle, and the adductor pollicis muscle. It does not supply the thenar muscles (flexor pollicis brevis, abductor pollicis brevis and opponens pollicis brevis) and the lateral two lumbrical muscles.

The ulnar nerve 20 sends sensory information to the brain from the medial one and a half fingers, i.e., the little finger and half of the ring finger, and the body of the hand below these fingers, on both the palmar and dorsal surfaces of the hand.

The area of numbness, pain or tingling 22 is often located in the hand on the side of the little finger and the outer side of the palm. Most common is the area of numbness, pain or tingling 22 located in the fourth and fifth fingers as shown in FIG. 1. The area of numbness, pain or tingling 22 may also be located in the arm, wrist or other areas of the hand.

Figure 2:
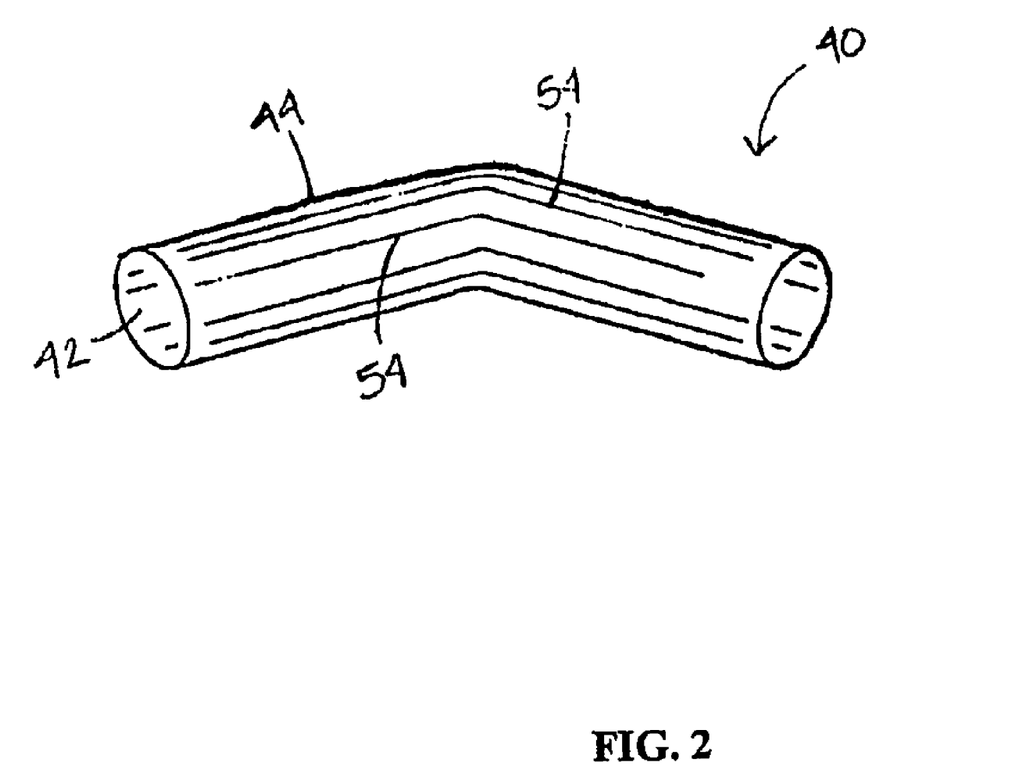
FIG. 2 shows a perspective view of a device for treating ulnar neuropathy of the presently disclosed embodiments.
Figure 3:
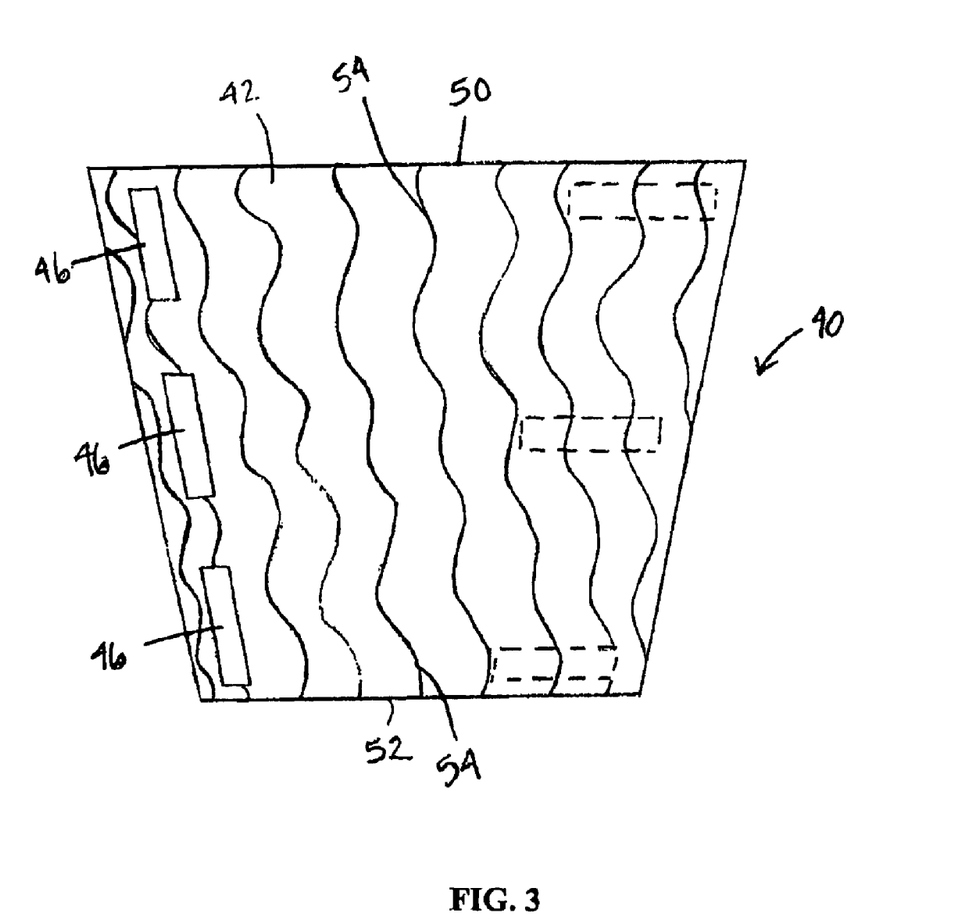
FIG. 3 shows a view of an inner face of a device for treating ulnar neuropathy of the presently disclosed embodiments.

A device for treating ulnar neuropathy is shown generally at 40 in FIG. 2. The orthotic device 40 or appliance includes an inner face 42, an outer face 44 and a plurality of mechanical fasteners 26 (FIG. 3). As shown in FIG. 2, in the device 40 has mild angulature at the elbow to place the ulnar nerve in position to promote healing and decrease pain. When the elbow is fully extended, the ulnar nerve is ever so slightly kinked. The elbow needs to be angled for the ulnar nerve to be fully at rest. The device 40 is angled to place the elbow in the resting position. A carrying angle 49 (FIG. 6) of the device 40 varies depending on the size of the device and length of the patient's arm and forearm. The carrying angle of the device can range from about 135 degrees to about 180 degrees. The carrying angle 49 allows the device 40 to provide semi-rigid immobilization of the elbow. Because the immobilization of the elbow is not completely rigid, the device 40 can be worn by a patient during the day or at night. The device 40 is contoured to the shape of the elbow. The device 40 is ambidextrous and can be applied to either the left arm or the right arm.

Figure 5:
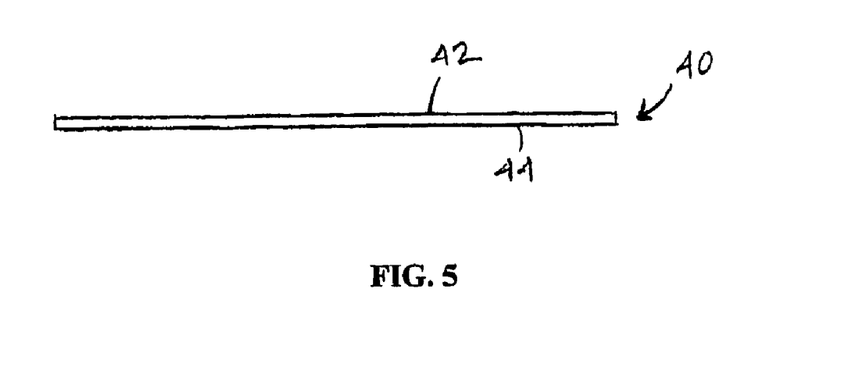
FIG. 5 shows a side view of a device for treating ulnar neuropathy of the presently disclosed embodiments.

FIG. 3 shows a view of the inner face 42 of the device 40 for treating ulnar neuropathy of the presently disclosed embodiments. As shown in FIG. 3, the device 40 has an irregular trapezoidal shape that is wider at an upper portion 50 and narrows at a lower portion 52. The trapezoidal shape of the device permits a snug fit on the upper arm and the narrower forearm of the patient. Because the device 40 closely but comfortably fits the arm and forearm, the device 40 can be worn under a patient's clothes, including long sleeve shirts. The thickness of the device 40 may vary and is based upon a combination of factors including the thickness required to provide the desired immobilization (i.e., a thicker device provides great immobilization), the use of the device 40 under clothing (i.e., a thinner device fits easier under clothing), and the feel of the device by the patient. (i.e., a bulky device is less likely to lead to patient compliance). Balancing these factors and others in the presently disclosed embodiments results in a device that provides semi-rigid immobilization and does not feel uncomfortable or obtrusive in use under the patient's clothing where the thickness is less than about one inch. FIG. 5 shows a view of the device 40 having a low-profile and minimal thickness. The device 40 is compact and lightweight so that shipping and stocking are not onerous. Those skilled in the art will recognize that devices having a range of thicknesses are contemplated within the spirit and scope of the presently disclosed embodiments.

The device 40 may be composed of a single material or a combination of materials to provide semi-rigid support of the elbow joint. The device 40 may be composed of synthetic rubbers, characterized by their resistance to chemicals and oxidation, including neoprene. The device 40 may be composed of non-porous rubberized materials to capture body heat, increases circulation and provides semi-rigid immobilization and support. The device 40 may be composed of vinyl which can be inflated. The device 40 may be composed of textiles including, but not limited to, polyester, cotton, nylon, alone or in combination with other natural or synthetic fibers, and other materials known to those skilled in the art. The device 40 can also include a facing material consisting of polyester batting or other synthetic or natural materials. The facing material also wicks away moisture and helps prevent skin irritation. The device 40 may be single layered or composed of multiple layers.

The inner face 42 is composed of or covered in a non-abrasive material to not irritate the skin of the patient. The non-abrasive material may also be hypoallergenic. Examples of the non-abrasive material of the inner face 42 include but are not limited to, pile, terry, fleece, flocked vinyl and other materials known to those skilled in the art.

The inner face 42 includes a plurality of mechanical fasteners 46 that engage the inner face 42 to the outer face 44 for closure over the arm of the patient. As shown in FIG. 3, the plurality of mechanical fasteners 46 are a hook or loop material used in engaging the device 40 to a patient's elbow are located along the left edge of the inner face. The device 40 may be closed by other mechanical fasteners including, but not limited, to buttons, snaps, zippers or other mechanical fasteners which operates on contact or pressure to mechanically engage two components. FIG. 3 shows three mechanical fasteners 46, but those skilled in the art will recognize that there can be a single mechanical fastener or any number of mechanical fasteners 46 used to the close the device 40.

Figure 4:
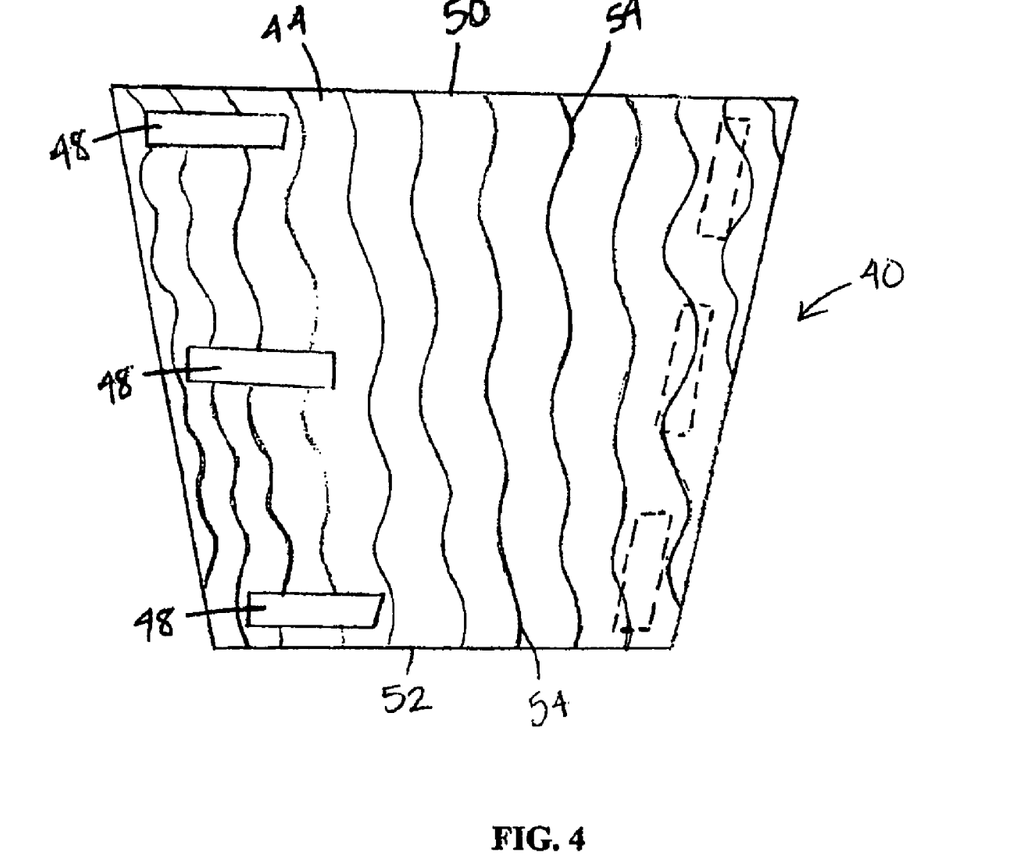
FIG. 4 shows a view of an outer face of a device for treating ulnar neuropathy of the presently disclosed embodiments.

FIG. 4 shows a view of the outer face 44 of a device for treating ulnar neuropathy of the presently disclosed embodiments. The outer face 44 includes the plurality of mechanical fasteners 46 that engage the outer face 44 to the inner face 42 for closure over the arm of the patient. As shown in FIG. 4, on the outer face 44, a plurality of mechanical fasteners 48 are a hook or loop material used in engaging the device 40 to a patient's elbow are located along the left edge of the outer face 33. The plurality of mechanical fasteners 48 on the outer face 44 are oriented in a direction opposite the direction of the plurality of mechanical fasteners 46 on the inner face 42. Having the mechanical fasteners 48 on the outer face 44 opposing the mechanical fasteners 46 on the inner face 42 provides for adjustment upon closing and permits the device 40 to be used by patents having varying arm shapes and sizes. As shown in FIG. 4, the mechanical fasteners 48 on the outer face 44 are arranged approximately perpendicular to the mechanical fasteners 46 on the inner face 42, an arrangement that facilitates a comfortable and snug fit of the device 40 on the arm of a patient. The device 40 may be closed by mechanical fasteners 48 other than hook and loop material including, but not limited, to buttons, snaps, zippers or other mechanical fasteners which operates on contact or pressure to mechanically engage two components. FIG. 4 shows three mechanical fasteners 48, but those skilled in the art will recognize that there can be a single mechanical fastener or any number of mechanical fasteners 48 used to the close the device 40.

The outer face 44 is composed of or covered in a material that may be form fitting, resilient, durable, water-resistant and/or hypoallergenic. Examples of the material of the outer face 44 include but are not limited to, nylon, polyester, cotton, pile, alone or in combination with other natural or synthetic fibers, and other materials know to those skilled in the art. The outer face 44 can also include a facing material consisting of polyester batting or other synthetic or natural materials.

Figure 6:
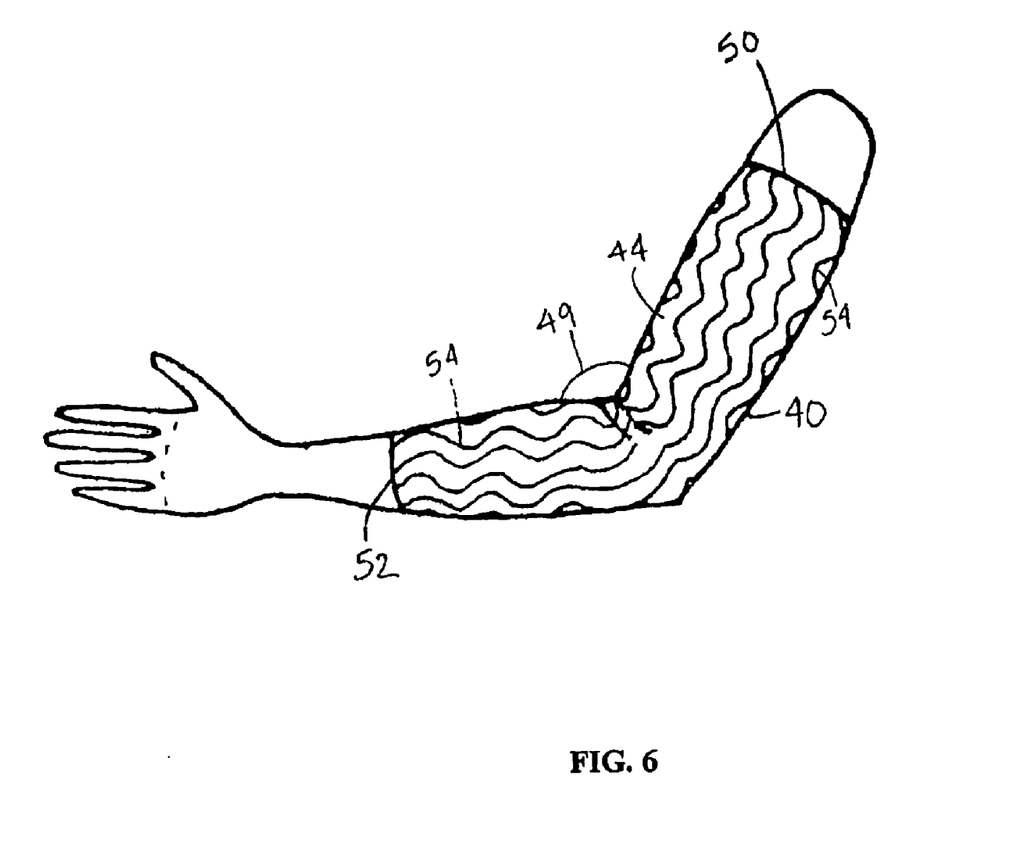
FIG. 6 shows an illustration of wearing a device for treating ulnar neuropathy of the presently disclosed embodiments on an arm.

In an embodiment, the inner face 42 and the outer face 44 include a plurality of channels 54 that run longitudinally along the device 40 as shown in FIG. 3, FIG. 4 and FIG. 6. The channels 54 promote circumferential flexibility with relative rigidity in the longitudinal direction. Serpentine channels 54 are effective in providing semi-rigid immobilization and maintaining circumferential flexibility. The channels may be any shape including straight, curved, discontinuous or other shapes and formations known to those skilled in the art. The material used to construct the inner face 42 and the outer face 44 maybe quilted or stitched together to promote circumferential flexibility with semi-rigid immobilization in the longitudinal direction.

The device 40 is easy to apply and the materials used encourage patient compliance. The device 40 can be made in a variety of sizes to accommodate adults, adults with larger arms, adolescents and children.

As shown in FIG. 6, the device 40 is placed on the patient by wrapping the device around the arm to extend above and below the elbow. In placing the device 40 on a patient, the elbow can be extended as far as comfort will allow and the open device 40 is placed on the patient's elbow with the lower portion 52 of the inner face 42 placed around the forearm, and the upper portion 50 of the inner face 42 placed around the upper arm. The wider upper portion 50 of the device 40 engages the upper arm, and the narrower lower portion 52 engages the forearm. The non-abrasive material of the inner face 42 is placed down over the patient's skin. After wrapping the device around the arm, the mechanical fasters 46 of the inner face 42 engage the mechanical fasteners 48 on the outer face 44. The device 40 does not impeded circulation and allows normal circulation in the arm and hand. One finger should be inserted under all edges for proper clearance. The device 40 should not be wrapped so tightly that circulation to hand is impeded.

The device 40 should be wrapped around the arm to extend above and below the elbow so that the angle of the elbow is constrained between about 135 degrees to about 180 degrees. The carrying angle 49 is the angle at which the device 40 positions the elbow. The carrying angle 49 of the device 40 varies depending on the size of the device and length of the patient's arm and forearm. The carrying angle 49 allows the device 40 to provide semi-rigid immobilization of the elbow joint. Because the immobilization of the elbow is not completely rigid, the device 40 can be worn by a patient during the day or at night.

The purpose of the angulation in the device 40 is to minimize the stress on the ulnar nerve. If the elbow is fully straightened to 180 degrees, the ulnar nerve is kinked which stresses the nerve. If the elbow is bent less than 135 degrees, the ulnar nerve is stretched, which interferes with the healing process. The device 40 should have a carrying angle 49 between about 135 degrees to about 180 degrees to bend the elbow to promote healing of the ulnar nerve because in this position the ulnar nerve is not stretched or stressed. A carrying angle between about 135 degrees and about 170 degrees promotes effective healing.

To remove or adjust the device 40, the mechanical fasteners 46 and 48 are disengaged and unfastened. To replace the device 40, extend the arm and place the device 40 inner side 42 toward and under the elbow 26 and fasten the mechanical fasteners 46 and 48 together. One finger should be inserted under all edges for correct clearance. The device 40 can be easily removed and replaced to treat wounds under the covered area.

In use, the complementary portions of a two-part mechanical fastener (e.g., hook-and-loop) are engaged around the arm of a patient. The hook-and-loop structure permits detachable attachment of the inner face 42 to the outer face 44. This detachable engagement permits the user to remove the device 40 from the arm and reinstall the device 40 in a looser or tighter orientation. A first part of the hook-and-loop fastener is the loop portion which presents for engagement a surface having multiple exposed fiber loops. The complementary part of the hook-and-loop fastener preferably includes a plurality of hooking stems formed and disposed to engage the fiber loops of the loop portion of the first part, in typical hook-and-loop fastener fashion. As used herein, "hook-and-loop fastener" means any two-part mechanical fastener which operates on contact or pressure to mechanically engage two components. A typical example of a hook-and-loop fastener using fibers and hooking stems is the fiber and hook combination material sold under the trademark Velcre®. Other suitable mechanical fastener assemblies will also suffice, so long as they achieve the characteristics of repeated mechanical engageability and separability without damage to the parts being joined and separated, and provide sufficient engagement force.

The first part of the hook-and-loop fastener has a plurality of exposed fiber loops, some of which are engaged by the complementary parts of the hook-and-loop fastener. The complementary parts of the hook-and-loop fastener in turn are formed as generally planar substrates having a plurality of hooking stems projecting outwardly therefrom. The hooking stems may be formed integrally with the substrate. Each hooking stem includes means for hooking an opposed surface (such as a loop material). The head may be any suitable shape or configuration to serve as a means to snag one or more of the fiber loops for engagement therewith upon contact. Suitable hooking structures and methods of their formation are disclosed in Melbye et al. U.S. Pat. No. 5,077,870, Chesley U.S. Pat. No. 5,505,747, Nestegard U.S. Pat. No. 4,894,060, and Thomas et al. U.S. Pat. No. 5,058,247, all these patents are hereby incorporated by reference herein.

The degree of adhesion achieved by the hook-and-loop fastener is a function of many variables. Some characteristics include the density of the hook-and-loop components, their relative sizes (e.g., height of loops and length of hooking stems) and the weight of the device 40. A low profile hook-and-loop fastener structure is desired. The engaging force can be increased by increasing the relative surface area of the hook-and-loop fastener (e.g., by increasing the size of the hooks on the second complementary part and the size of the hooks on the other complementary part or by other means such as changing densities of the hooking stems or head sizes, etc.).

Figure 7:
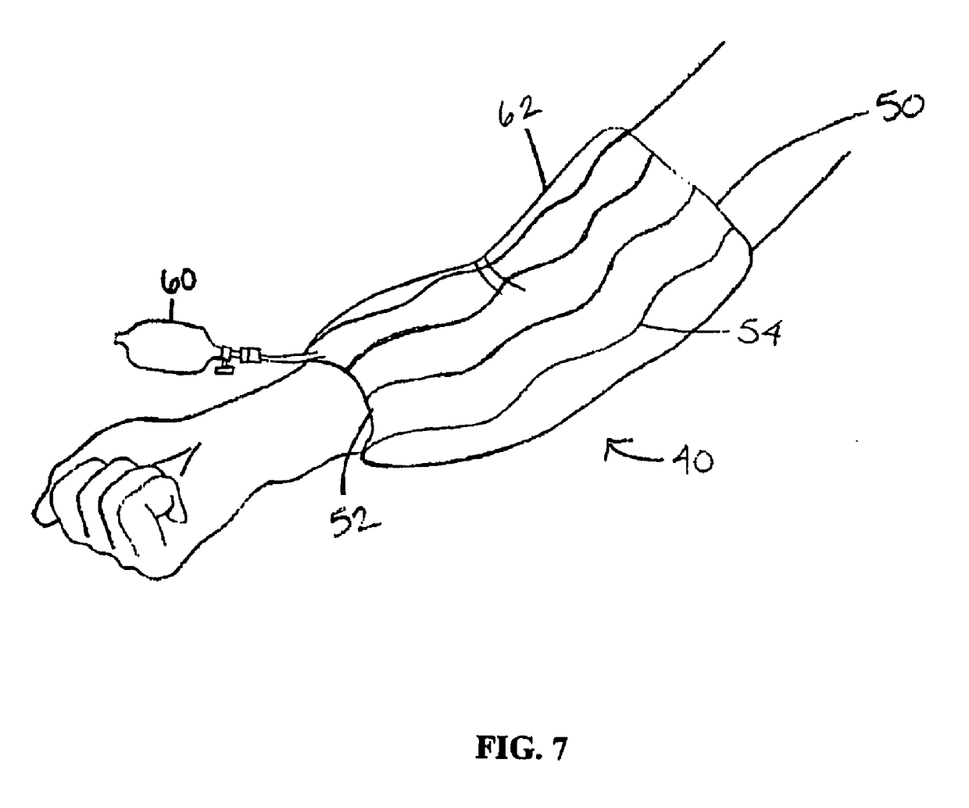
FIG. 7 shows a view of an embodiment of a device for treating ulnar neuropathy having a inflatable portion.

In an embodiment shown in FIG. 7, the device 40 is inflatable so that it could be inflated at night to be stiffer when patients are less likely to move their arm. The inflatable device has adjustable pressure so that during the daytime the device can be made more flexible and less rigid and during the nighttime the device can made less flexible and more rigid. The inflatable embodiment provides longitudinal semi-rigidity while being circumferentially wrappable to conform to the user's arm and elbow. In an inflatable embodiment, there is an inflation valve that controls inflation. In an inflatable embodiment, there is a maximum pressure release valve to ensure that the device does not exceed a maximum pressure. A hand pump 60 may be attached to a bladder 62 to inflate or deflate the bladder as needed by the patient. As shown in FIG. 7, the entire device 40 is the air bladder 62. In other embodiments, the air bladder 62 forms only a portion of the device.

The inflatable device may be composed of vinyl or other impermeable materials that allow for inflation and deflation. In an inflatable embodiment, the inner face and the outer face could be fused together along the outer edges and along longitudinal curvy ribs to form serpentine channels that would fill with air when the device was inflated. The channels allow the device to expand as inflated to a desired thickness. A release valve ensures that the air bladder is not over-inflated to cause undue pressure on the arm and to maintain the low profile of the device. In an inflatable embodiment, the inner face may be flocked for user comfort.

The inflation device stabilizes the elbow joint, allowing the ulnar nerve to heal free from further injury that could be caused without a supportive device. The device is designed to increase stability without restricting mobility. The air bladder is inflated to hold the elbow in the degree of extension desired. The greater the degree of extension, the more inflation in the air bladder. Once the amount of air pressure necessary for either stabilization or immobilization has been determined, the device 40 can be removed and put back on without changing the air pressure in the air bladder.

The air bladder is slowly inflated to increase the pressure against the upper and lower arm. This will hold the contracted arm in the extended range of motion position. The inflatable air bladder maintains the arm in an extended position without undo pressure on the flexors above and below the elbow joint. The air bladder allows continuous motion of the elbow joint by resisting the flexion contractors with resultant relation of the flexor muscles. There is minimal pressure against the soft tissue and the device does not constrict the blood flow nor cause undo pressure on the nerves.

In an embodiment, an exoskeleton frame is provided for use with device 40. The exoskeleton frame can be positioned around the device 40 to provide more rigid support. Surrounding the outer face and providing a means to set the elbow in a multiplicity of fixed positions, the exoskeleton frame is secured to the outer face by straps having hook and loop material surrounding the outer face of the device. The exoskeleton frame may be a deformable mesh or an external-fixation frame.

The exoskeleton frame is provided with a plurality of interchangeable support portions for setting an elbow of a patient in a variety of fixed positions. The exoskeleton may have a hinged support portion that can be set to maintain the elbow in a desired position. The exoskeleton may have a rigid support portion. The exoskeleton may have a polycentric support portion that allows the exoskeleton frame to be locked in a variety of fixed positions.

The apparatus and method for treating ulnar neuropathy disclosed herein is safe, tolerable, effective, comfortable, non-invasive, affordable and readily available.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An apparatus for treating ulnar neuropathy comprising:
an inner face for engaging a person's arm with an upper end terminating above the person's elbow and a lower end terminating below the elbow;

a carrying angle provided between the upper end and the lower end, the carrying angle being fixed within a range of about 135 degrees and about 170 degrees such that the upper end and lower end are movable with respect to each other only within the fixed range of about 135 degrees and about 170 degrees;

a plurality of mechanical fasteners along an edge of the inner face;

an outer face having channels to promote circumferential flexibility; and a plurality of mechanical fasteners on the outer face positioned to oppose the plurality of mechanical fasteners on the inner face;

wherein the apparatus is contoured to the shape of the elbow and provides semi-rigid immobilization of the elbow within the fixed carrying angle range of about 135 degrees to about 170 degrees.

2. The apparatus of claim 1 wherein the channels are serpentine to provide semi-rigid immobilization and circumferential flexibility.

3. The apparatus of claim 1 further comprising channels in the inner face.

4. The apparatus of claim 1 wherein the plurality of mechanical fasteners on the inner face and outer face are opposing components of a hook and loop material.

5. The apparatus of claim 1 wherein the plurality of mechanical fasteners on the outer face are arranged approximately perpendicular to the plurality of mechanical fasteners on the inner face.

6. The apparatus of claim 1 wherein the carrying angle is provided so as to place the ulnar nerve in position to promote healing and the resolution of pain.

7. The apparatus of claim 1 further comprising an inflatable air bladder located between the inner face and the outer face.

8. The apparatus of claim 1 further comprising an exoskeleton frame to limit the movability of the upper end and lower end with respect to each other, such that the upper end and lower end are fixed with respect to each other, thereby providing rigid support of the elbow at a fixed carrying angle.

9. An apparatus for supporting an elbow in a desired position comprising:

an inner face for engaging a person's arm with an upper end terminating above the person's elbow and a lower end terminating below the elbow;

a carrying angle provided between the upper end and the lower end, the upper end and lower end being movable with respect to each other within a fixed carrying angle range between about 135 degrees and about 170 degrees;

at least one hook and loop fastener located along an edge of the inner face;

a plurality of channels in the inner face to provide support along a length of the inner face; and an outer face having channels to promote circumferential flexibility and at least one hook and loop fastener positioned to oppose the least one hook and loop fastener on the inner face;

wherein the apparatus is contoured to the shape of the elbow and provides semi-rigid immobilization of the elbow within the fixed carrying angle range.

10. The apparatus of claim 9 wherein the channels are serpentine.

11. The apparatus of claim 9 wherein the plurality of mechanical fasteners on the outer face are arranged approximately perpendicular to the plurality of mechanical fasteners on the inner face.

12. The apparatus of claim 9 wherein the fixed carrying angle range is provided so as to place the ulnar nerve in position to promote healing and decrease pain.

13. The apparatus of claim 9 further comprising an inflatable air bladder located between the inner face and the outer face.

14. The apparatus of claim 9 further comprising an exoskeleton frame to limit the movability of the upper end and lower end with respect to each other, such that the upper end and lower end are fixed with respect to each other, thereby providing rigid support of the elbow at a fixed carrying angle.

15. A method of treating ulnar neuropathy comprising:

placing an inner face of the apparatus according to claim 1 in contact with an arm of a patient;

wrapping the device around the arm to extend above and below the elbow;

engaging mechanical fasters on the inner face of the device with mechanical fasteners on the outer face;

tightening the device to support the elbow while allowing normal circulation in the arm; and semi-rigidly immobilizing the angle of the elbow such that the elbow is provided with a range of motion within the fixed carrying angle range of between about 135 degrees to about 180 degrees;

thereby treating ulnar neuropathy.

16. The method of claim 15 wherein the device further comprises an inflatable air bladder located between the inner face and the outer face, and the method further comprises inflating the air bladder to prevent the range of motion of the elbow and hold the elbow at a fixed angle between about 135 degrees to about 180 degrees.

17. The method of claim 15 wherein the device further comprises further comprising attaching a frame to the device to provide rigid support of the angle of the elbow.

18. A method of treating ulnar neuropathy comprising:

placing an inner face of the apparatus according to claim 9 in contact with an arm of a patient;

wrapping the device around the arm to extend above and below the elbow;

engaging the at least one hook and loop fastener on the inner face of the device with the at least one hook and loop fastener on the outer face;

tightening the device to support the elbow while allowing normal circulation in the arm; and semi-rigidly immobilizing the angle of the elbow such that the elbow is provided with a range of motion within the fixed carrying angle range of between about 135 degrees to about 180 degrees;

thereby treating ulnar neuropathy.

* * * * *